(12) United States Patent
Saito

(10) Patent No.: US 7,486,400 B2
(45) Date of Patent: Feb. 3, 2009

(54) PLASMON RESONANCE STRUCTURE WITH METAL NANOPARTICLE LAYERS

(76) Inventor: Takao Saito, c/o Saito Research Institute of Technology Co., Ltd., Tokyo Tech Yokohama Ventura Plaza #W402, 4259-3 Nagatsuta-cho Midoriku, Yokohama - city, Kanagawa (JP)

( * ) Notice: Subject to any disclaimer, the term of this patent is extended or adjusted under 35 U.S.C. 154(b) by 210 days.

(21) Appl. No.: 11/424,785

(22) Filed: Jun. 16, 2006

(65) Prior Publication Data

US 2006/0274315 A1 Dec. 7, 2006

(30) Foreign Application Priority Data

Jun. 16, 2005 (JP) ............................. 2005-176899

(51) Int. Cl.
*G01N 21/27* (2006.01)
(52) U.S. Cl. ...................... 356/445; 356/301
(58) Field of Classification Search ............... 356/445
See application file for complete search history.

(56) References Cited

U.S. PATENT DOCUMENTS

| 7,193,719 B2 * | 3/2007 | Meehan et al. | 356/445 |
| 2006/0197952 A1 * | 9/2006 | Chen et al. | 356/445 |
| 2008/0198376 A1 * | 8/2008 | Poponin | 356/301 |

FOREIGN PATENT DOCUMENTS

| JP | 11-326193 | * 11/1999 |
| WO | PCT/DK2004/000830 | * 11/2004 |

OTHER PUBLICATIONS

Lin, Chii-Wan, et al., "Design and fabrication of an alternating dielectric multi-layer device for surface plasmon resonance sensor", Mar. 2006, Sensors and Actuators B 113, pp. 169-176.*

* cited by examiner

*Primary Examiner*—L. G Lauchman
*Assistant Examiner*—Rebecca C Slomski

(57) ABSTRACT

The electric-field enhancement effect by plasmon resonance is improved by favorably controlling the plasmon resonances in the thickness direction and in the direction orthogonal thereto. The plasmon resonance structure body comprises alternately stacked layers of metal nanoparticle layers and dielectric particle layers. The metal nanoparticle layers have a structure as such that the nano-sized fine particles of Au, Ag, Al, or the like, form metallic domains disposed at proper distance from each other along the direction orthogonal to the stacking direction of the layers. Used as the dielectric particle layer is, for instance, $SiO_2$. The plasmon resonance in the thickness direction of the direction orthogonal thereto of the plasmon resonance structure body can be controlled by changing the particle diameter or the distance among the particles of the metal nanoparticles and the dielectric particles, or by changing the number of the stacked layers.

6 Claims, 4 Drawing Sheets

PLASMON RESONANCE STRUCTURE WITH METAL NANOPARTICLE LAYERS

BACKGROUND OF THE INVENTION

1. Field of the Invention

The present invention relates to a plasmon resonance structure body, and more specifically, it relates to a method of controlling the plasmon resonance thereof.

2. Background Art

In the near-field optics, the utilization of electric-field enhancement effect is conceived, and studies are being made on its application to various fields such as telecommunication, recording media, or the like (see non-patent reference 1 below). The electric-field enhancement effect can be realized by forming fine particles several to several hundred nanometers in size (which are referred to simply hereinafter as "nano-sized fine particles"), and by using the localized surface plasmon that generates in the vicinity thereof. The nano-sized fine particles can be formed generally by a chemical method, for example, a sol-gel process, and are used in a three-dimensionally dispersed state in a film. FIG. 4 shows an example comprising nano-sized metallic fine particles 902 dispersed randomly in the dielectric film 900.

Non-patent reference 1: OYO-BUTURI, Vol. 73, No. 10 (2004) "Propagation and control of surface plasma politon", pp. 1275-84.

It is known that, when light is incident to nano-sized fine particles from the thickness direction of a film, localized surface plasmon is distributed in the direction orthogonal to the light. Accordingly, in order to control the localized surface plasmon, different modes, i.e., in the thickness direction and inside the plane orthogonal to the thickness direction, must be taken into consideration. However, the plasmon resonance structure body obtained by the chemical process above is in such a state that nano-sized fine particles are randomly distributed in three dimensions; hence, the plasmon resonance cannot be controlled for independent modes in the film thickness direction and in the direction orthogonal thereto. Accordingly, it has been unfeasible to achieve efficient improvement on the plasmon enhanced electric-field effect.

SUMMARY OF THE INVENTION

The invention has been made focused on the point above, and an objective of the invention in an embodiment is to favorably control the plasmon resonances in the thickness direction and in the direction orthogonal thereto. Another objective of the invention in an embodiment is to control plasmon resonance to improve the electric-field enhancement effect.

In order to achieve one or more of the objectives above, according to an aspect of the invention, dielectric particle layers composed of dielectric particles are interposed between nanoparticle layers constructed by metal nanoparticles.

The aspect above and other aspects, characteristics, and advantages of the invention are made clear by the detailed description and the attached figures below.

According to an embodiment of the invention, plasmon resonance is controlled by the particle diameter and the spacing among the metal nanoparticles and the dielectric particles, and the number of stacked layers. Thus, plasmon resonance can be favorably controlled, and its electric-field enhancement effect can be improved by the invention.

For purposes of summarizing the invention and the advantages achieved over the related art, certain objects and advantages of the invention have been described above. Of course, it is to be understood that not necessarily all such objects or advantages may be achieved in accordance with any particular embodiment of the invention. Thus, for example, those skilled in the art will recognize that the invention may be embodied or carried out in a manner that achieves or optimizes one advantage or group of advantages as taught herein without necessarily achieving other objects or advantages as may be taught or suggested herein.

Further aspects, features and advantages of this invention will become apparent from the detailed description of the preferred embodiments which follow.

BRIEF DESCRIPTION OF THE DRAWINGS

These and other features of this invention will now be described with reference to the drawings of preferred embodiments which are intended to illustrate and not to limit the invention. The drawings are oversimplified for illustrative purposes and are not to scale.

DETAILED DESCRIPTION OF THE INVENTION

Best modes for implementing the invention are described in detail below by way of examples. The examples are not intended to limit the present invention. In the present disclosure where conditions and/or structures are not specified, the skilled artisan in the art can readily provide such conditions and/or structures, in view of the present disclosure, as a matter of routine experimentation.

EXAMPLES

Example 1

Figure 1A:
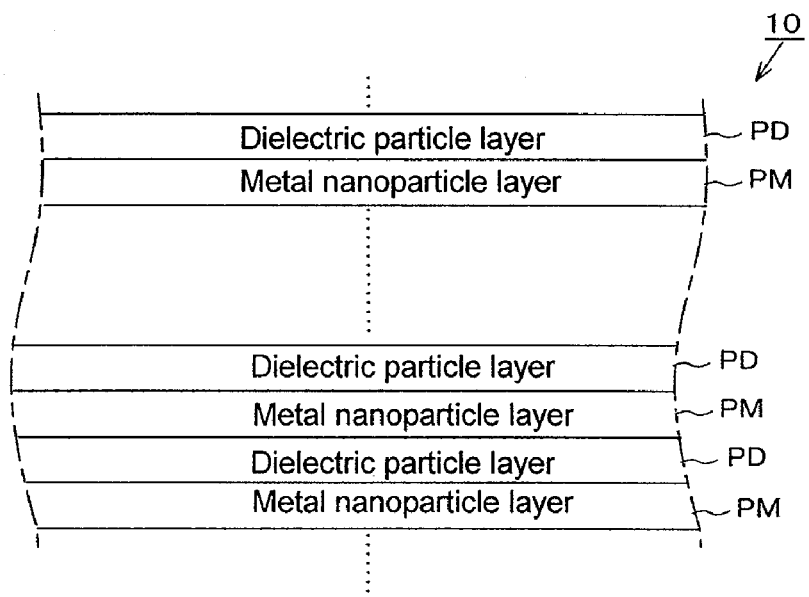
FIG. 1A is a cross section view showing the stacked layer structure of a plasmon resonance structure body according to a first embodiment of the invention.

A first example is explained firstly by making reference to FIGS. 1A-1C and 2A-2C. FIG. 1A shows the cross section of the stacked layer structure of a plasmon resonance structure body 10 according to the present embodiment. Referring to the figure, the plasmon resonance structure body 10 is composed of alternately stacked layers of metal nanoparticle layers PM and dielectric particle layers PD. The metal nanoparticle layer PM has a structure wherein the nano-sized fine particles of Au, Ag, Al, or the like form metallic domains disposed at proper distance from each other along the direction orthogonal to the stacking direction of the layers. As the dielectric particle layer PD, for example, $SiO_2$ or the like is used.

Figure 1B:
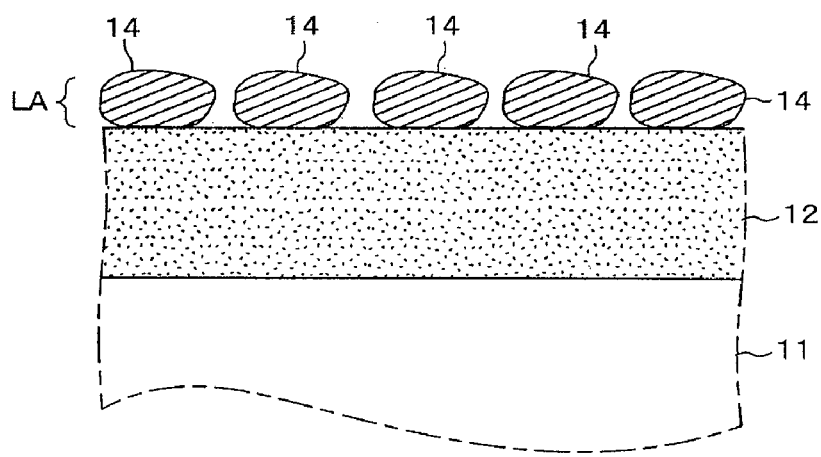
FIGS. 1B and 1C are diagrams showing cross section view of the main production process steps thereof.
Figure 1C:
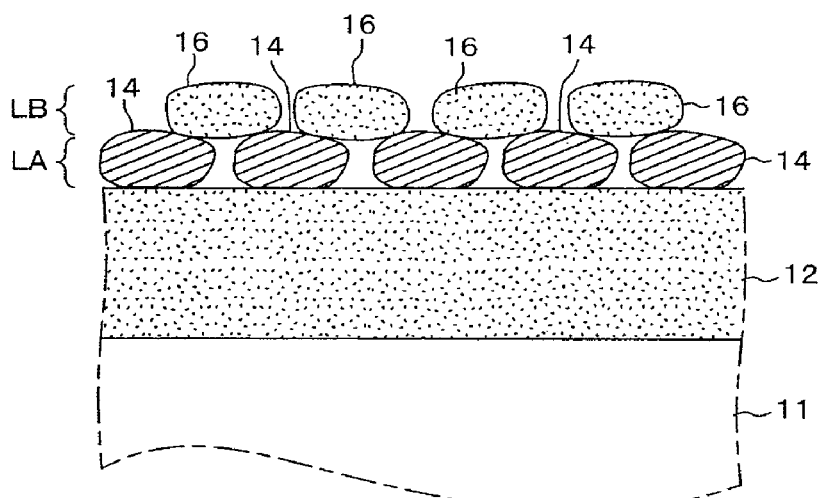
Figure 2A:
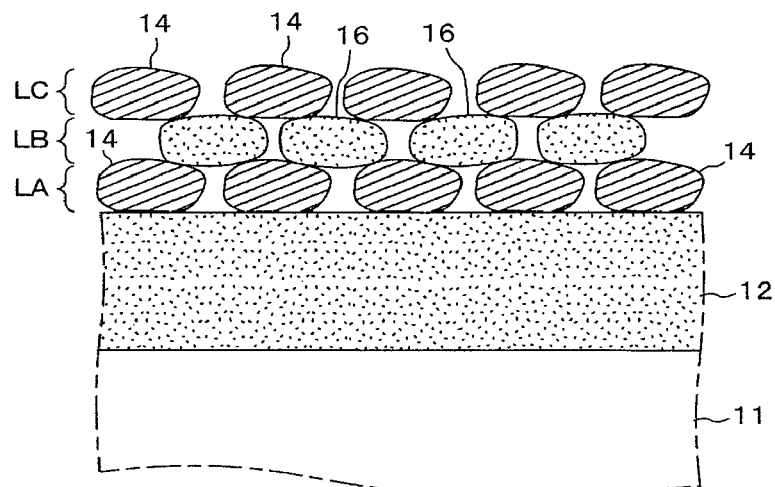
FIGS. 2A to 2C are each a cross section view showing the main production process step of the plasmon resonance structure body according to the first embodiment above.
Figure 2B:
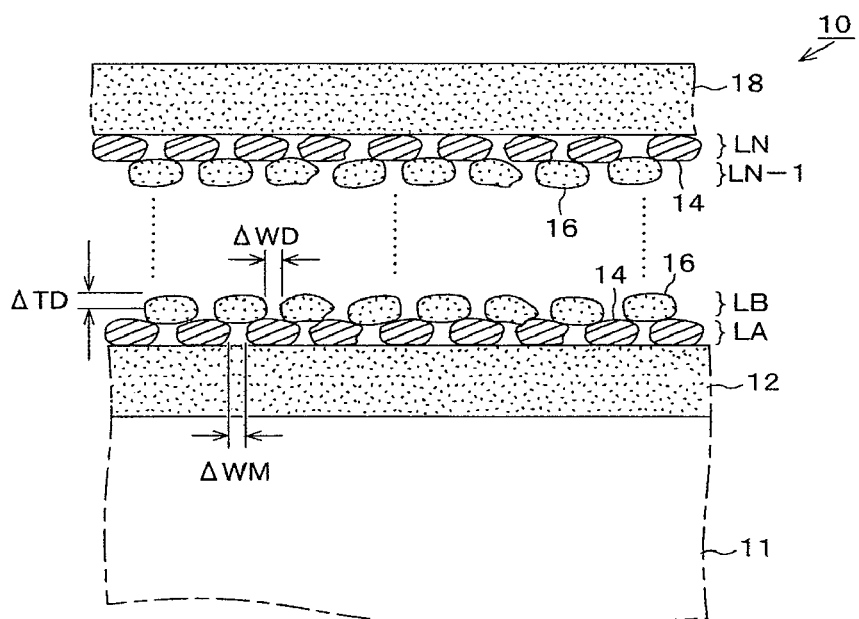
Figure 2C:
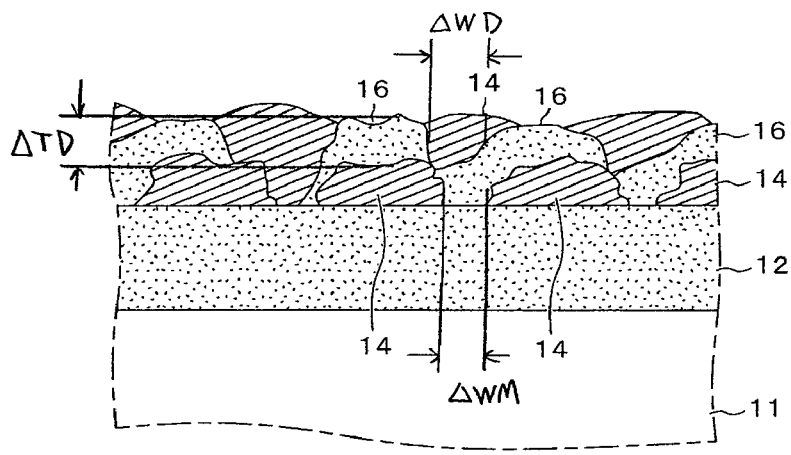

The particle layer structure above is formed, for instance, by a method shown in FIGS. 1B and 1C, and in FIGS. 2A to 2C. In this example, the plasmon resonance structure body 10 is composed of alternately stacking the metal nanoparticle layers (PM or 14) and the dielectric particle layer (PD or 16), each layer having a thickness of about 10 nm to about 30 nm, for example. In general, the resultant intensity of plasmon resonance is related to the particle size, and the greater the size of metal nanoparticles and dielectric particle, the higher the absorbance becomes (as described below, the degree of generating plasmon can be detected by measuring absorbance). Thus, although the size of metal nanoparticles and dielectric particle may generally be in the range of about 10 nm to about 30 nm, the size can be about 50 nm or greater (e.g., less than 100 nm). The plasmon resonance structure body 10 is typically sandwiched between dielectric layers 12, 18 (using $SiO_2$, for example) each having a thickness of about 40 nm to about 80 nm, for example. The dielectric layer 12 is typically formed on a substrate 11 such as a glass substrate having a thickness of about 1 mm to about 2 mm, for example. The plasmon resonance structure body 10 has a thickness of about 1 mm to about 2 mm, for example. In general, the higher the number of layers (PM and PD), the more the plasmon resonance can be improved.

A first layer (layer A: LA) and a last layer (layer N (N is an add number): LN) of the Plasmon resonance structure body are typically the metal nanoparticle layers (PM or 14). Thus, typically, layers LA, LC, LE, . . . , and LN are the metal nanoparticle layers (PM or 14), whereas layers LB, LD, LF, . . . , and L(N−1) are the dielectric particle layer (PD or 16). Each of Layers LA, LC, LE, . . . , LN need not be of the same type (e.g., the same material, the same thickness, the same structure, etc.). However, for obtaining strong electric-field enhancement effect, each layer is preferably of the same type. Likewise, each of Layers LB, LD, LF, . . . , L(N−1) need not be of the same type (e.g., the same material, the same thickness, the same structure, etc.). However, for obtaining strong electric-field enhancement effect, each layer is preferably of the same type.

Referring to FIG. 1B, the dielectric layer 12 is formed on the principal plane of a glass substrate 11 by sputtering or a like method. Subsequently, a metal nanoparticle layer LA made of metal nanoparticles 14 is formed on the dielectric layer 12, for instance, by sputtering or a like method. In general, in the initial stage of film formation, the metallic film does not cover the entire principal plane of the substrate, but metal particles adhere to form island-like portions. With progressive sputtering, fine domains of the metal particles combine with the neighboring domains to grow into metal nanoparticles or metal domains 14, which are disposed at predetermined spacing from each other. The states of the particles are thus controlled by following the film quality control based on Thornton diagram, which is the fundamental of film deposition technology.

Subsequently, as shown in FIG. 1C, a dielectric particle layer LB made of dielectric particles 16, such as of $SiO_2$ or the like, is formed on the metal nanoparticle layer LA by means of sputtering or the like. For both of the metal nanoparticles 14 and the dielectric particles 16, the particle diameter and the spacing among the particles can be controlled by adjusting the sputtering time and the sputtering temperature, respectively. As shown in FIG. 1C, each layer may not be clearly separated from each other and may contain both of the metal nanoparticles 14 and the dielectric particles 16. However, each layer is continuously but separately produced by a separate process, and as a result, the metal nanoparticle layer contains more metal nanopartcles than dielectric particles, and the dielectric particle layer contains more dielectric particles than metal nanoparticles.

Each layer (LA, LB, . . . , LN) can be formed by any other suitable PVD methods, suitable CVD methods, or suitable electric beam lithography. Sputtering is preferable since it is relatively easy to control the growth of particles and configurations.

Then, metal nanoparticle layer LC made of metal nanoparticles 14 is formed on the surface of the dielectric particle layer LB. By thus alternately stacking the metal nanoparticle layer and the dielectric particle layer, a structure as shown in FIG. 2B is finally obtained. Furthermore, a dielectric layer 18 (e.g., a thickness of about 40 nm to about 80 nm) for sealing purpose is formed on the uppermost metal nanoparticle layer LN. Thus is obtained a plasmon resonance structure body 10.

In the figures referred above, the particles 14 and 16 are each shown in uniform size to facilitate understanding of the structure, but in fact, they are believed to be formed in an island-like shape that is extended in the horizontal direction as shown in FIG. 2C.

As described above, the structure according to the present example comprises alternately stacked layer structure of the metal nanoparticle layers LA, LC, . . . , each of which containing the metal nanoparticles 14 arranged at predetermined spacing in the horizontal plane, and the dielectric particle layers LB, LD, . . . , each of which containing the dielectric particles 16. Accordingly, in the horizontal direction, the spacing ΔWM between the metal nanoparticles 14 and the spacing ΔWD between the dielectric particles 16 (see FIG. 2B) can be adjusted by controlling the growth of the particles. Furthermore, in the vertical direction, the distance between the metal nanoparticle layers LA, LC, . . . , can be adjusted by controlling the thickness ΔTD of the dielectric particles 16.

ΔWD, ΔWM, and ΔTD can be measured using a scanning electron microscope (SEM). ΔWD and ΔWM each represent a minimum distance observed, and ΔTD represents a maximum thickness observed. The configuration of a metal nanoparticle layer can be defined based on the number of particles in a square 100 nm in side length and ΔWM (since the shape of particles are generally uniform and nearly spherical), and the configuration of a dielectric particle layer can be defined based on ΔWD and ΔTD (since the number of particles is not readily countable with SEM observation).

Then, a sample of a plasmon resonance structure body 10 having a structure as follows was fabricated to measure plasmon. The measurement of plasmon was carried out by irradiating a propagating light to the sample, and the light absorbance of the sample was measured by a spectrophotometer. The light absorbance changes when the propagated light is converted into plasmon. Thus, the degree of generating plasmon can be detected by measuring absorbance. The present invention will be further explained with reference to the following experiments. The numerals indicated in the experiments can very by ±10% to ±100% (±20%, ±50%, ±80%, and any numbers therebetween) in other experiments with modified conditions.

(1) Experiment 1

A dielectric layer 12 made of $SiO_2$ was formed at a thickness of 80 nm on a glass substrate 11. Subsequently, a metal nanoparticle layer LA was formed by using Ag particles as the metal nanoparticles 14 having an average particle diameter of 15 nm and in which twenty-four particles were distributed in a square 100 nm in side length. Then, a dielectric particle layer LB was formed by using $SiO_2$ particles as the dielectric particles 16 having an average particle diameter of 15 nm, and in which the particles were distributed at an average spacing of 3 nm.

The particle distribution for the metal nanoparticles 14 was described by the number of particles contained within a square area 100 nm in side length. However, for the dielectric particles 16, the description was made by the average spacing among the particles because they were uncountable due to their amorphous morphology, and because they were dispersed in a nearly constant spacing.

Subsequently, five metal nanoparticle layers LC, LE, ..., and four dielectric particle layers LD, LF, ..., were formed alternately under the conditions similar to those stated above. Thus, six metal nanoparticle layers were formed in total, and five dielectric particle layers were formed interposed between them to provide an alternately stacked layer structure as a whole. For sealing purpose, a dielectric layer 18, which was made of $SiO_2$, was formed at a thickness of 80 nm on the metal nanoparticle layer provided as the uppermost layer. On measuring absorbance of the plasmon resonance structure body thus obtained, a maximum peak absorbance of Abs=1.006 was obtained at a wavelength $\lambda$=447 nm.

(2) Experiment 2

In Experiment 1, six layers of metal nanoparticle layer and five layers of dielectric particle layer were formed, but in the present Experiment 2, two layers each were added for both layers to form eight layers of metal nanoparticle layer and seven layers of dielectric particle layer. The other conditions were the same as those in Experiment 1 above. On measuring absorbance of the plasmon resonance structure body thus obtained, a maximum peak absorbance of Abs=1.520 was obtained at a wavelength $\lambda$=440 nm. That is, the absorbance increased as compared with the case of Experiment 1.

(3) Experiment 3

A dielectric layer 12 made of $SiO_2$ was formed at a thickness of 80 nm on a glass substrate 11. Subsequently, a metal nanoparticle layer LA was formed by using Ag particles having an average particle diameter of 15 nm as the metal nanoparticles 14, in which twenty-four particles were distributed in a square 100 nm in side length. This procedure was the same as in the experiments above. Then, in the present experiment, a dielectric particle layer LB was formed by using $SiO_2$ particles having an average particle diameter of 10 nm as the dielectric particles 16, which were distributed at an average spacing of 2 nm. That is, dielectric particles 16 having a slightly smaller particle diameter and somewhat narrower spacing were used. Subsequently, nine layers of metal nanoparticle layers LC, LE, ..., and eight layers of dielectric particle layers LD, LF, ..., were formed alternately under the same conditions to above, to finally obtain an alternately stacked layer structure having ten layers of metal nanoparticle layer with nine layers of dielectric particle layer interposed between them. For sealing purpose, a dielectric layer 18, which was made of $SiO_2$, was formed at a thickness of 80 nm on the metal nanoparticle layer provided as the uppermost layer. On measuring absorbance of the plasmon resonance structure body thus obtained, a maximum peak absorbance of Abs=1.758 was obtained at a wavelength $\lambda$=463 nm.

(4) Experiment 4

A dielectric layer 12 made of $SiO_2$ was formed at a thickness of 40 nm on a glass substrate 11. Subsequently, a metal nanoparticle layer LA was formed by using Ag particles having an average particle diameter of 10 nm as the metal nanoparticles 14, in which thirty particles were distributed in a square 100 nm in side length. Then, a dielectric particle layer LB was formed by using $SiO_2$ particles having an average particle diameter of 10 nm as the dielectric particles 16, which were distributed at an average spacing among particles of 2 nm. Subsequently, additional four metal nanoparticle layers LC, LE, ..., and three dielectric particle layers LD, LF, ..., were formed alternately under the conditions similar to those stated above.

Thus, five metal nanoparticle layers were formed in total, and four dielectric particle layers were formed interposed between them to provide an alternately stacked layer structure as a whole. For sealing purpose, a dielectric layer 18, which was made of $SiO_2$, was formed at a thickness of 40 nm on the metal nanoparticle layer provided as the uppermost layer. On measuring absorbance of the plasmon resonance structure body thus obtained, a maximum peak absorbance of Abs=0.668 was obtained at a wavelength $\lambda$=480 nm.

(5) Experiment 5

A dielectric layer 12 made of $SiO_2$ was formed at a thickness of 40 nm on a glass substrate 11. Subsequently, a metal nanoparticle layer LA was formed by using Ag particles having an average particle diameter of 20 nm as the metal nanoparticles 14, in which seventeen particles were distributed in a square 100 nm in side length. Then, a dielectric particle layer LB was formed by using $SiO_2$ particles having an average particle diameter of 20 nm as the dielectric particles 16, which were distributed at an average spacing of 5 nm. Subsequently, additional four metal nanoparticle layers LC, LE, ..., and three dielectric particle layers LD, LF, ..., were formed alternately under the conditions similar to those stated above.

Thus, five metal nanoparticle layers were formed in total, and four dielectric particle layers were formed interposed between them to provide an alternately stacked layer structure as a whole. For sealing purpose, a dielectric layer 18, which was made of $SiO_2$, was formed at a thickness of 80 nm on the metal nanoparticle layer provided as the uppermost layer. On measuring absorbance of the plasmon resonance structure body thus obtained, a maximum peak absorbance of Abs=1.100 was obtained at a wavelength $\lambda$=446 nm. By comparing the present results with those of Experiment 4, it can be understood that the absorbance increases with decreasing peak wavelength by doubling the average particle diameter.

Conclusively, the experiment results show that:

(a) the absorbance increases with increasing number of metal nanoparticle layers; and (b) the absorbance increases with increasing particle diameter of the metal nanoparticles and the dielectric particles.

The plasmon resonance in the thickness direction and in the direction orthogonal thereto can be favorably controlled by changing the particle diameter and the spacing of the metal nanoparticles and dielectric particles, or the number of stacked layers. Accordingly, the electric-field enhancement effect of plasmon resonance can be thereby improved. Furthermore, since the strength is improved, noble metals generally used in the art may be replaced by base metals such as copper, aluminum, or the like as shown in Experiment 6 below.

(6) Experiment 6

A sample was fabricated using Cu (copper) as the metal nanoparticles 14 and $SiO_2$ for the dielectric particles, without changing the particle size from that of Experiment 5. Thus was obtained a sample having five layers of metal particle layer and four layers of dielectric particle layer as a whole, which yields an absorbance of 0.368 at a wavelength of 655 nm.

(7) Experiment 7

A sample was fabricated in the same manner as in Experiment 6, except for changing the number of layers to fifteen layers of metal particle layer and fourteen layers of dielectric particle layer. The sample was found to yield an absorbance of 0.873 at a wavelength of 612 nm.

Thus, the same tendency of increasing absorbance with increasing number of layers for the metal nanoparticle layer, which was conceived on Experiments 1 and 2 above, was also observed in the case using Cu.

Example 2

Figure 3:
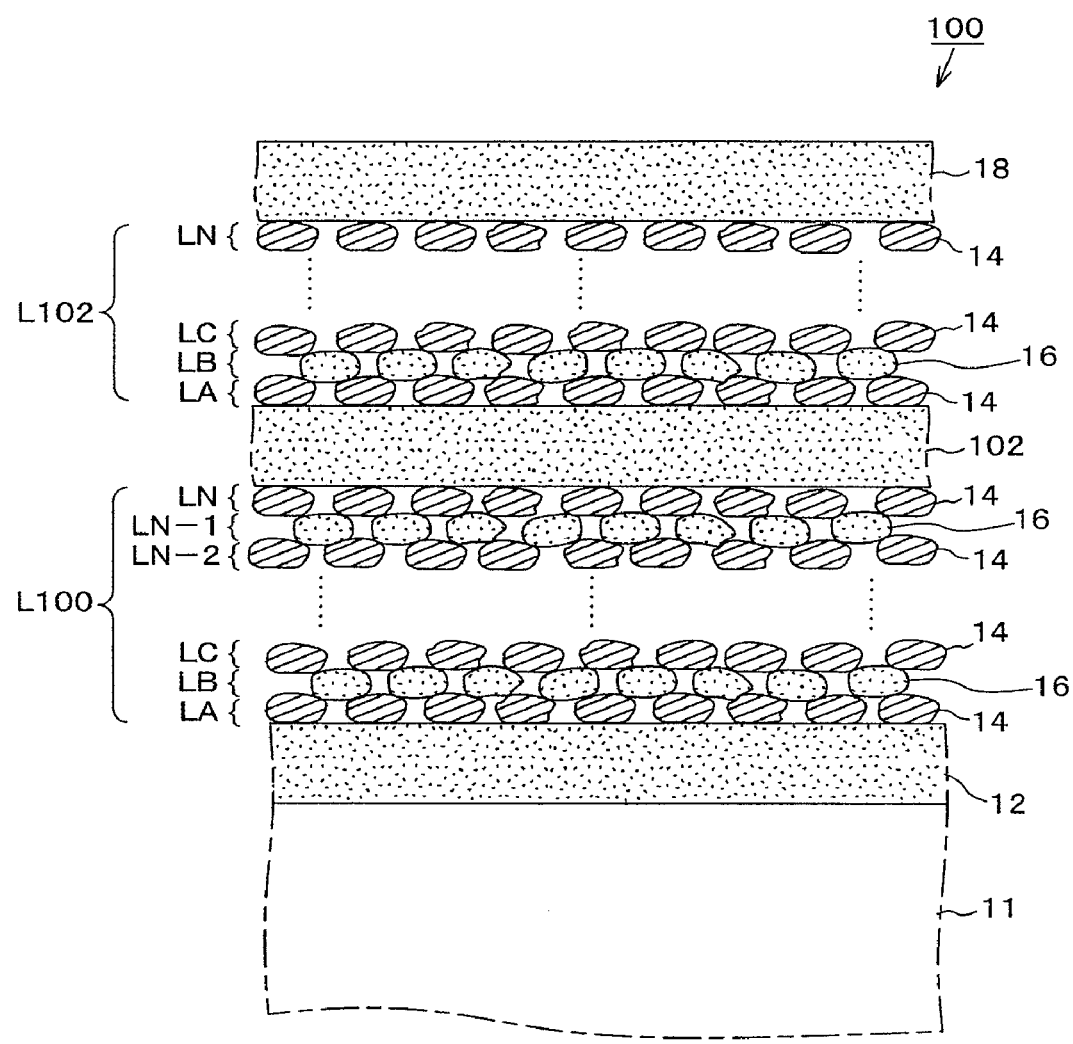
FIG. 3 is a cross section view showing the stacked layer structure of a plasmon resonance structure body according to a second embodiment of the invention.
Figure 4:
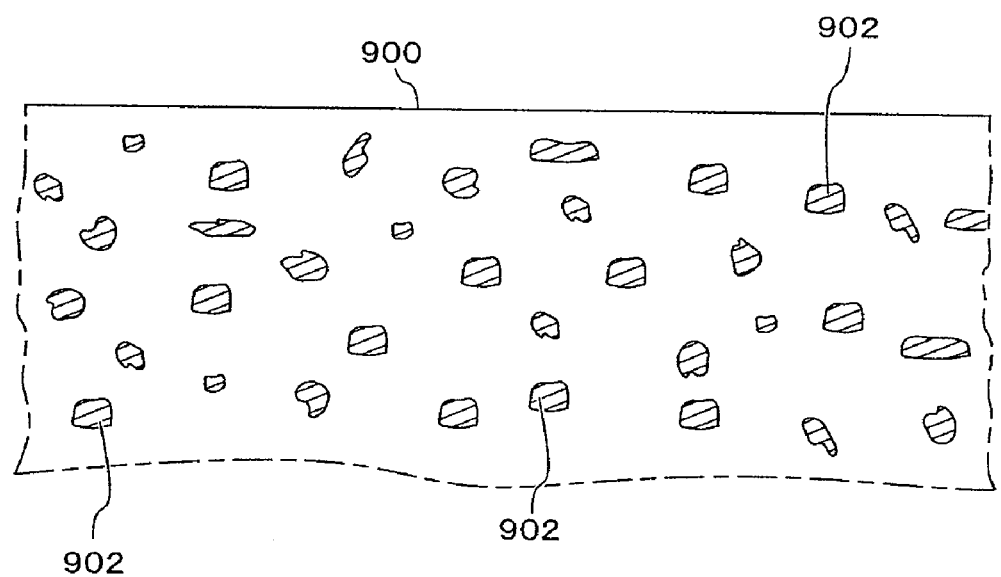
FIG. 4 is a cross section view showing an example of a plasmon resonance structure body based on related art.

Referring to FIG. 3, Example 2 according to the invention is described below. In the present example, plural structures obtained in Example 1 were further laminated to obtain the structure. Referring to FIG. 3, a dielectric layer 12 made of SiO$_2$ was formed on the principal plane of the glass substrate 11 by means of sputtering or the like. Subsequently, metal nanoparticle layers LA, LC, . . . LN made of metal nanoparticles 14, and dielectric particle layers LB, LD, . . . , LN−1, made of dielectric particles 16, were formed alternately on the dielectric layer 12. Thus was formed a nano-laminate body L100.

Subsequently, a dielectric layer 102 was formed on the nano-laminate body L100, and another nano-laminate body L102 was formed thereon. The nano-laminate body L102 had the same constitution as that of the nano-laminate body L100 described hereinbefore. Then, a dielectric layer 18 for sealing purpose was formed on the nano-laminate body L102 to obtain a plasmon resonance structure body 100. Thus, similar effects can be obtained by further stacking plural laminates with dielectric layers interposed between the metal nanoparticle layers and the dielectric particle layers.

Other Examples

The invention is not only limited to the examples described above, and various changes and modifications can be made so long as they do not depart from the spirit and the scope of the invention. For instance, the materials and the fabrication processes above are simple examples, and other known materials having the same effect or other fabrication processes are also applicable. Furthermore, in the direction of forming the metal nanoparticle layers and dielectric particle layers, sputtering method was referred as an example, however, other vapor phase deposition technologies including vapor deposition method, CVD method, or the like may be used to form the particle layers.

In accordance with the invention, the plasmon resonance of a plasmon resonance structure body can be favorably controlled in the thickness direction and in the direction orthogonal thereto; thus, the invention is suitably applied to various types of sensors, optical circuit devices, or the like, because the electric-field enhancement effect is improved.

The present application claims priority to Japanese Patent Application No. 2005-176899, filed Jun. 16, 2005, the disclosure of which is incorporated herein by reference in its entirety.

It will be understood by those of skill in the art that numerous and various modifications can be made without departing from the spirit of the present invention. Therefore, it should be clearly understood that the forms of the present invention are illustrative only and are not intended to limit the scope of the present invention.

What is claimed is:

1. A plasmon resonance layered structure comprising:
   metal nanoparticle layers constructed by metal nanoparticles; and
   dielectric particle layers composed of dielectric particles wherein the metal nanoparticle layers and the dielectric particle layers are alternately deposited to constitute the layers structure that generates plasmon resonances.

2. A plasmon resonance layered structure as claimed in claim 1, wherein the metal nanoparticles are disposed distant from each other in the direction in which localized plasmon is distributed, provided that the spacing between the metal nanoparticles is two times as large as the particle diameter of the metal nanoparticles or smaller.

3. A plasmon resonance layered structure as claimed in claim 2, wherein the metal nanoparticles are disposed distant from each other at a spacing equivalent to the particle diameter of the metal nanoparticles or smaller.

4. A plasmon resonance layered structure as claimed in claim 1, wherein the dielectric particles have approximately the same particle diameter as that of the metal nanoparticles.

5. A plasmon resonance layered structure as claimed in claim 1, wherein the metal nanoparticles and the dielectric particles have a size of less than 100 nm.

6. A plasmon resonance layered structure as claimed in claim 5, wherein each layer of the metal nanoparitcle layers and the dielectric particle layers has a thickness of less than 100 nm.

* * * * *